United States Patent [19]

Brody

[11] 4,414,693

[45] Nov. 15, 1983

[54] OPTICAL DEVICES FOR USE IN MOISTURE LADEN ATMOSPHERE

[76] Inventor: Samuel S. Brody, 5 Saxony Rd., Pittsford, N.Y. 14534

[21] Appl. No.: 260,643

[22] Filed: May 4, 1981

[51] Int. Cl.³ .............................................. A61F 9/02
[52] U.S. Cl. ..................................... 2/435; 350/588; 55/16
[58] Field of Search ......................... 2/435, 436, 426; 350/66, 61; 428/913; 55/16; 260/544 F

[56] References Cited

U.S. PATENT DOCUMENTS

| | | | |
|---|---|---|---|
| 2,317,658 | 4/1943 | Welsh | 2/435 |
| 2,537,275 | 1/1951 | Malcolm, Jr. | 2/436 |
| 3,488,215 | 1/1970 | Shepherd et al. | 2/435 X |
| 3,506,635 | 4/1970 | Anderson | 260/544 FX |
| 3,735,559 | 5/1973 | Salemme | 55/16 |

*Primary Examiner*—Peter P. Nerbun

*Attorney, Agent, or Firm*—M. Lukacher

[57] ABSTRACT

Fogging by the condensation of water vapor on optically transmissive surfaces of optical devices, such as the lens of goggles, is prevented by means of a transparent hydrophylic polymer integrated therewith and disposed in the moisture laden environment. A perfluorosulfonic acid polymer, such as is sold under the trademark Nafion by Du Pont, is used. The polymer is attached to the surface of the lens which faces the wearer of the goggles, as by being laminated to the lens. The polymer provides a transparent regeneratable dessicant, even though it is attached to the non-permeable lens, and removes water before it can condense as droplets to fog the lens. There also may be characteristics of the hydrophylic polymer other than that of a dessicant which is significant in the fog prevention (e.g. contact angle of water droplets on the surface).

13 Claims, 8 Drawing Figures

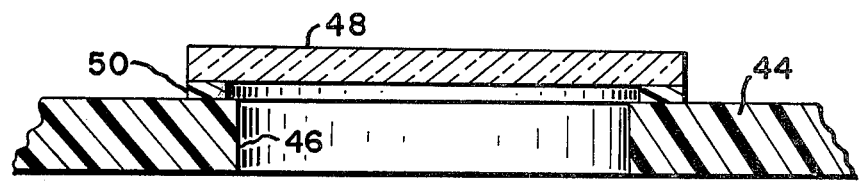
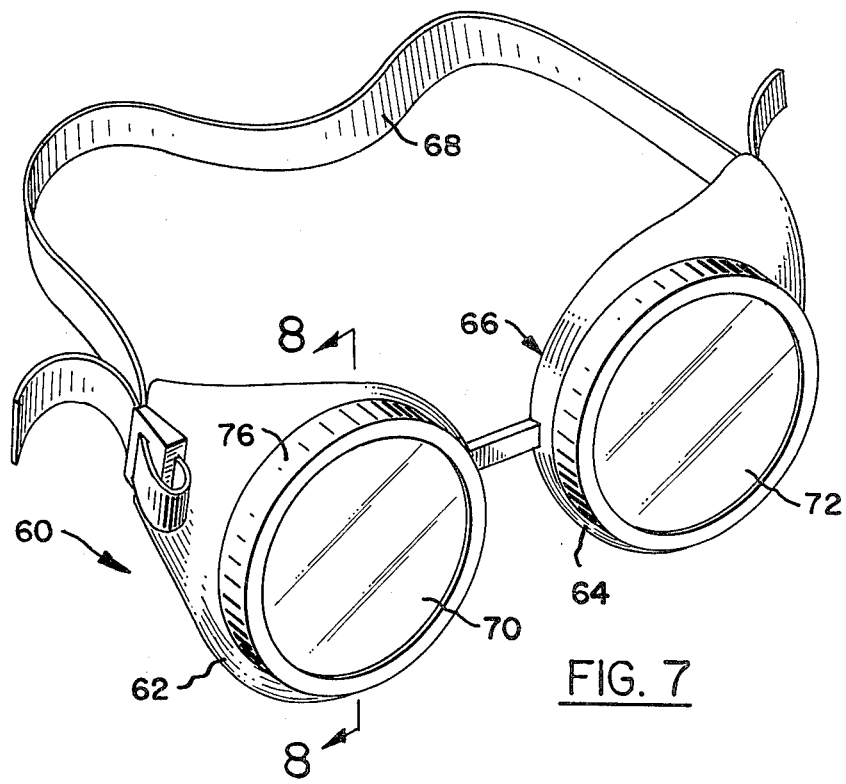
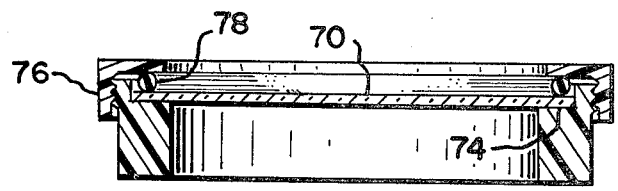

OPTICAL DEVICES FOR USE IN MOISTURE LADEN ATMOSPHERE

DESCRIPTION

The present invention relates to optical devices, which are subject to fogging when used in moisture laden environments, and in which fogging is prevented.

The invention is especially suitable for use in goggles for preventing of fogging of the lens. The term "goggles", as used herein includes face masks for sports or industrial application, for example as ski masks or gas masks as well as helmets and other eye wear. Although the lens is conventionally non-refracting, the term lens includes refracting as well as non-refracting bodies.

Fogging of optical devices, such as lenses, mirrors and devices in which they are incorporated, has long been a problem. This is particularly the case with goggles, where moisture can build up in the area of the face which the goggles enclose. Fogging on the inside surface of the lens which faces towards the face of the wearer is more serious than the fogging of the outside surface of the lens, since the face is a continuous source of water vapor, and is often warmer than the surrounding environment. Attempts at fogging prevention have included chemical treatment, double lenses, forced air, and electrically heated lenses. Forced air devices are not practical in toxic environments where the goggles must be sealed. They are also expensive. Chemical treatment, such as lens coating, which is effective (such as soap) has not been found to be permanent. Permanent lens coatings have not been found to be effective. Long-term exposure to moisture or large extremes in temperature between the moisture laden area and the lens result in fogging in spite of the use of double walled lenses in the goggles or permanent treatment of the lens.

It has been discovered, in accordance with the invention, that a hydrophylic polymer material may be used for fogging prevention in goggles and other optical devices which are exposed to moisture laden atmospheres and on which moisture, and even in aerosol form (droplets of water), may form. This material is a perfluorosulfonic acid polymer. It is sold under the trademark Nafion by the E. I. Du Pont DeNemours and Company of Wilmington, Del. The polymer is available in tubing and sheets and has been used in tubular form for drying purposes. The material sold under the Nafion tradename is a copolymer of tetrafluoroethylene and monomers such as perfluoro-3, 6-dioxa-4-methyl-7-octensulfonic acid. The polymer and its applications, particularly for drying purposes, is described in the following patents and publications: Skarstrom et al, U.S. Pat. No. 3,735,558, issued May 29, 1973; Baker, "Measuring Trace Impurities In Air By Infrared Spectrosopy At 20 Meters Path and 10 Atmospheres Pressure", American Industrial Hygiene Assoc. Journal, November, 1974, page 735; and Foulger, "Drier For Field Use In The Determination Of Trace Atmospheric Gases", Analytical Chemistry, Vol. 51, No. 7, June, 1979, page 1089. The process for making the polymer is believed to be described in Anderson, U.S. Pat. No. 3,506,635, issued Apr. 14, 1970, with additional information in a paper, "Nafion, an Electrochemical Traffic Controller" by Daniel J. Vaughan in DuPont's Innovation Magazine, Series 4, No. 3, 1973, p. 10–13.

It has been found that the hydrophylic properties of Nafion prevent the surface of an optical device from fogging when temperature of the Nafion body is below the dew point of air in the atmosphere with which it is in contact. The Nafion body may be applied and attached to a non-porous surface, such as the lens of the goggles, and nevertheless functions as a transparent regeneratable dessicant.

Accordingly, it is an object of the present invention to provide improved optical devices, which are used in a moisture laden atmosphere, and which are protected against fogging.

A further object of the invention is to provide improved goggles wherein fogging of the viewing area, which is caused by condensation of moisture built up within the region enclosed by the goggles, is prevented.

It is a still further object of the invention to provide improved goggles in which fogging of the lens is prevented by a hydrophylic polymer which can be attached to the lens of the goggles to provide a transparent regeneratable dessicant.

It is a still further object of the invention to provide improved goggles in which fogging of the lens is prevented without ventilating the goggles so as to facilitate use of the goggles in a toxic environment.

It is a still further object of the invention to provide improved goggles capable of operating in an environment where fogging due, not only to water vapor condensate but also to water droplets, may be prevented.

It is a still further object of the invention to provide improved goggles in which fogging is prevented without the need for forced air flow, chemical dessicants, heated lenses or means for establishing a pressure differential between the area enclosed by the goggles and the ambient, as necessary in devices such as described in the above referenced Skarstrom et al. patent.

Briefly described, an optical device embodying the invention has an optically transmissive body with a surface facing a water vapor or aerosol containing atmosphere. At least a portion of the body, which has the surface as a part thereof, consists of a perfluorosulfonic acid polymer. This polymer may be laminated to the lens of an optical device, such as goggles. Alternatively, the polymer may be used to seal an opening in the frame of the goggles which provides an interface between the moisture laden enclosed area of the goggles and the ambient.

The foregoing and other objects, features and advantages of the invention as well as presently preferred embodiments thereof will become more apparent from a reading of the following description in connection with the accompanying drawings in which:

FIG. 6 is a fragmentary sectional view taken along the line 6—6 in FIG. 5 showing a membrane mounted in sealing relationship with an opening on the frame;

FIG. 7 is a perspective view of goggles in accordance with still another embodiment of the invention; and FIG. 8 is a fragmentary sectional view taken along the line 8—8 in FIG. 7 and showing one of the eye cups of the goggles having a sheet of transparent hydrophylic polymer material providing the lens thereof.

Figure 1:
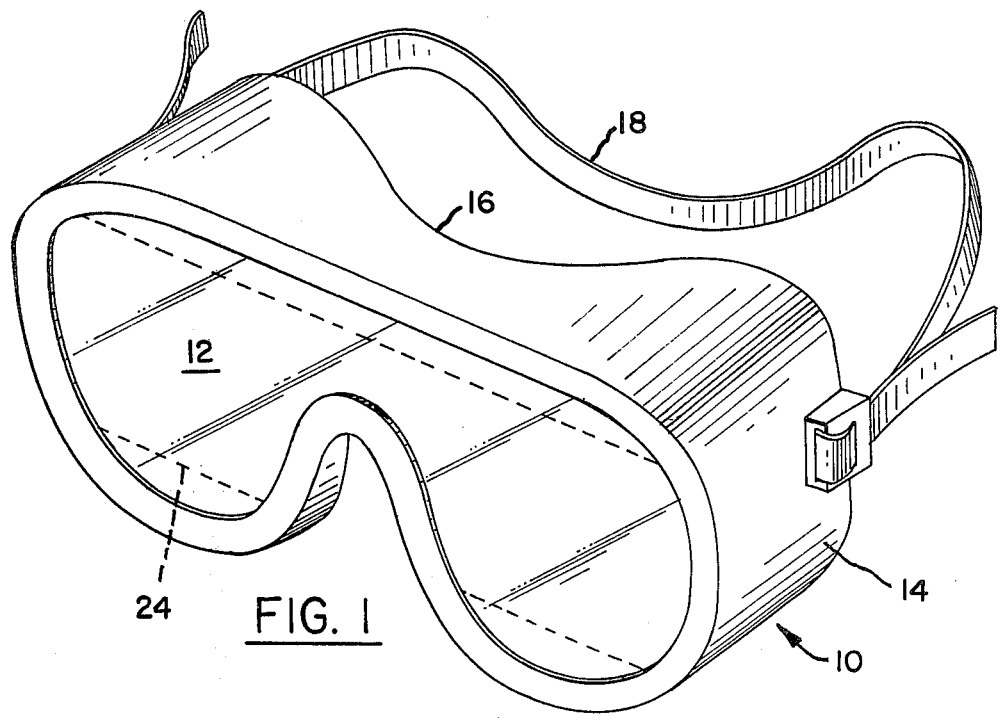
FIG. 1 is a perspective view of goggles embodying the invention.
Figure 2:
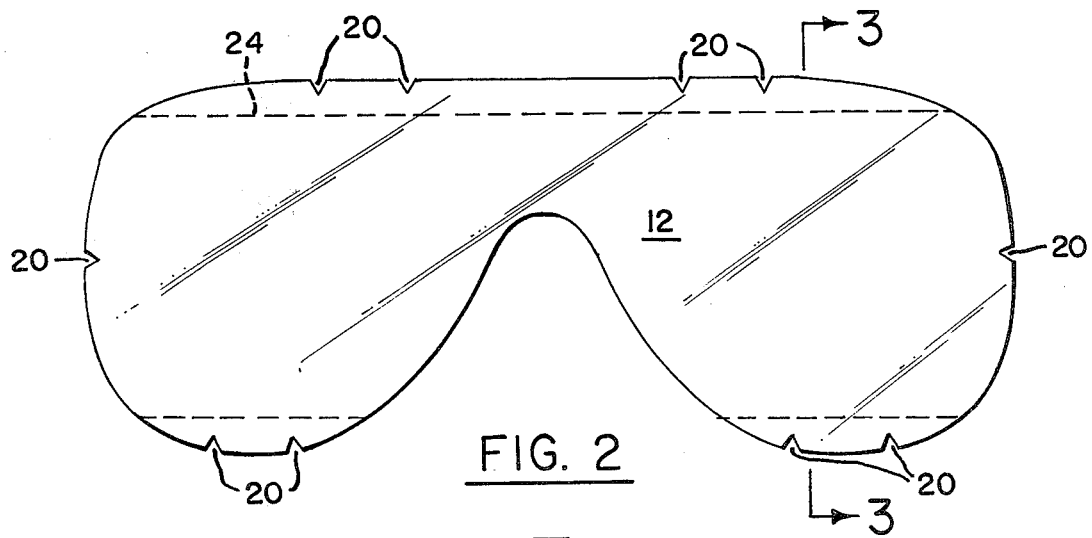
FIG. 2 is a front view of the lens of the goggle shown in FIG. 1 removed from the frame thereof.
Figure 3:
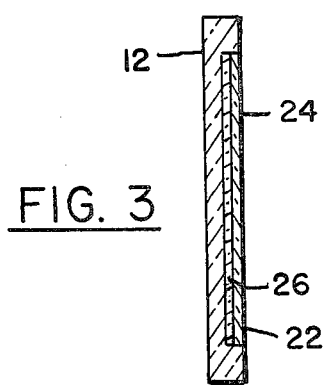
FIG. 3 is a sectional view of the lens taken along the line 3—3 in FIG. 2.

Referring first to FIGS. 1 through 3, there is shown goggles 10. A single lens 12 is supported in a frame 14. A rim 16 of pliant material is adapted to be placed against the face and provides a seal with the face of the wearer. Due to perspiration, the area enclosed by the goggles becomes a moisture laden atmosphere and may even contain water in aerosol (droplet) form. The temperature differential between the ambient and the enclosed area will cause the lens to fog, particularly when the goggles are worn outdoors in cold weather. An elastic band 18 holds the goggles 10 on the face, further assuring that the area of the face closed by the goggles is sealed.

The lens 12 has notches 20 for positioning and securing the lens 12 in the frame 14. The lens may be made of clear plastic, for example, polycarbonate. The inner surface 22 of the lens which faces the face of the wearer and defines, in part, the area enclosed by the goggles consists of a sheet or membrane 24 of hydrophylic polymer. The sheet is made entirely of perfluorosulfonic acid polymer. Preferably a sheet of Nafion is used. The sheet is of about the same dimensions as the lens so that it extends substantially up to the frame. The sheet 24 is laminated to the lens so as to provide a transparent unitary structure. Lamination is preferred, although other methods for attaching the sheet may be used, for example clear epoxy glue, sonic welding, gaskets and mechanical hold-down mechanisms.

A presently preferred method of attaching the sheet 24 is to use, for the sheet, Du Pont Nafion, type 117 (7 mil thickness, 1,100 equivalent weight, ion exchange membrane in the H+ form). A sheet of transfer tape 26 is placed on the lens. This tape may be Scotch Brand No. 465, 2 mil thickness tape, which is an acrylic based tape. A pressure of 4,000 psig is applied with heat (200° F.). The sheet 24 is then laminated into the polycarbonate lens 12.

In attaching the hydrophylic sheets to the inside surface of the lens, other transfer tapes which are transparent may be used, for example, Scotch Brand No. Y9469, 5 mil Isotac transfer tape, which is made entirely of acrylic polymer.

Notwithstanding that the polycarbonate lens 12 is non-porous, the hydrophylic polymer, nevertheless, operates as a transparent regeneratable dessicant. It absorbs the water, whether in vapor or aerosol droplet form, so rapidly that any condensate which would normally form on the surface 22, due to cooling and supersaturation of the moisture content of the air in the area enclosed by the goggle, is absorbed before the condensate forms an obstruction to visability. Also contact angle of water with the hydrophylic polymer may prevent the appearance of fog. The frame of the goggles need not be ventilated, although ventilation may be preferred, if possible in order to make the wearer more comfortable.

Figure 4:
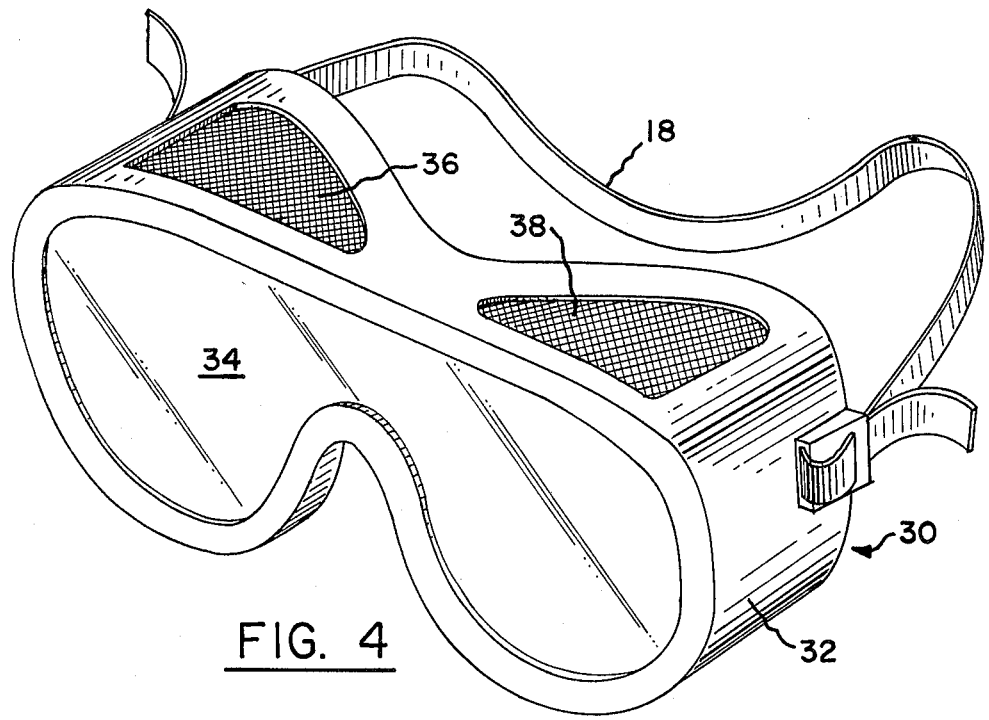
FIG. 4 is a perspective view of goggles in accordance with another embodiment of the invention wherein ventilation is provided in the frame of the goggles.

FIG. 4 shows ventilated goggles 30. These goggles have a frame 32 and a lens 34 with a hydrophylic polymer inner surface. Such a lens is made as described in connection with FIGS. 2 and 3. The frame has triangular shaped openings 36 and 38 closed by an open-weave fabric or mesh which provides for ventilation. The ventilation of the polymer surface and release of moisture (desorption) occurs.

Figure 5:
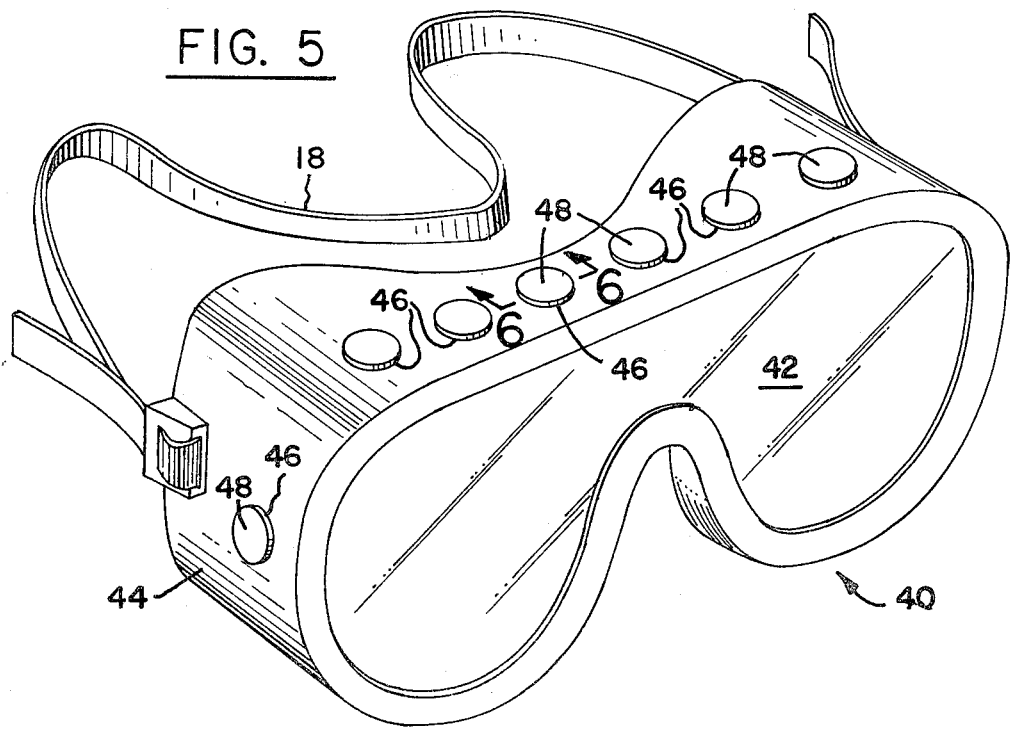
FIG. 5 is a perspective view of goggles in accordance with still another embodiment of the invention wherein moisture is effectively pumped through the frame via openings sealed by membranes of hydrophylic polymer.

The goggles 40 shown in FIG. 5 also has a lens 42 which may be fabricated as described in connection with FIGS. 2 and 3. A frame 44 holds the lens 42, and a band 18 enables the goggles to be worn on the head of the wearer. A row of openings 46 in the frame 44 extend inwardly from the edge defined by the intersection of the lens 42 and the frame 44. As shown in FIG. 6, each of these openings is sealed by a membrane 48 of hydrophylic polymer, preferably Du Pont Nafion, which is attached in sealing relationship with the opening 46 by a ring 50 of transfer tape. The tape may be double sided adhesive tape which laminates the Nafion membrane (discs of Nafion may be used) to the frame 44 around the openings 46. The goggles 40 are especially desirable for use in toxic environments since the area enclosed by the goggles remains sealed. The membranes 48 act as a pump to remove the water vapor from the area into the surrounding ambient air. No forced air is needed, nor is any pressure differential.

The lens 42 may, as described above, be provided with a sheet of Nafion on the inside surface thereof as described in connection with FIGS. 2 and 3. When the Nafion membrane sealed holes in the frame are used, as shown in FIG. 5, the lens 42 may be a conventional lens without the Nafion inner surface.

Referring to FIGS. 7 and 8, there is shown goggles 60 having separate eye cups 62 and 64 held together by a support structure which provides a frame 66. A band of elastic material 68 may be connected to the frame 66 and mounts the goggles 60 on the wearers head. Each eye cup 62 and 64 has a lens 70 and 72.

As shown in FIG. 8, the lens 70 is a sheet of transparent hydrophylic polymer, preferably Nafion, or other perfluorosulfonic acid polymer. The same material as used to provide the inner surface of the lens 12 may be used. The lens 70 is therefore a sheet or membrane of hydrophylic polymer. It is disposed on a step 74 at the outer end of the eye piece 62. A threaded ring 76 presses an O-ring 78 down upon the sheet 70 and holds it securely in place. The O-ring 78 also provides a seal and ensures that the area of the goggles between the face and the sheet 70 is sealed. Other means for attachment of the retaining ring 76 may be used, for example, the ring may be provided with a flange which snaps fits into a groove in the cup 62.

Other variations, modifications, and optical devices which embody the invention will undoubtedly suggest themselves to those skilled in the art. Accordingly, the foregoing description should be taken as illustrative and not in a limiting sense.

I claim:

1. An optical device having an optically transmissive body with a surface facing a water vapor or aerosol atmosphere, at least a portion of said body which has said surface as a part thereof consisting of a hydrophylic perfluorosulfonic acid polymer for fogging prevention.

2. Invention as set forth in claim 1 wherein goggles provide said device, said goggles having a lens and a frame for supporting said lens upon the face of the wearer of said goggles, said lens being said optically transmissive body, said surface being on the side of said lens which faces the face of the wearer.

3. The invention as set forth in claim 2 wherein said portion is a sheet of said polymer attached to said lens to provide at least a portion of said surface.

4. The invention as set forth in claim 3 wherein said sheet is of about the same dimensions as said lens so that said sheet extends substantially up to said frame.

5. The invention as set forth in claim 2 wherein said lens consists entirely of said polymer.

6. The invention as set forth in claim 2 wherein said frame comprises a pair of cups, said lens being separate lenses in different ones of said cups, said lenses each having a separate sheet of said polymer attached to the sides thereof facing the face of the wearer or being a sheet consisting of said polymer.

7. The invention as set forth in claim 2 wherein said frame has means therein providing communication between the ambient and the interior of said goggles for ventilating said interior and said surface.

8. Invention as set forth in claim 2 wherein said frame has a plurality of openings therein, a plurality of membranes of said polymer on said frame over said openings, and means attaching said membranes to said frames to seal said openings.

9. The invention as set forth in claim 3 wherein said sheet and said lens are laminated to each other.

10. The invention as set forth in claim 9 wherein said lens consists of transparent plastic, a layer of acrylic polymer coextensive with said sheet, and said lens, layer and sheet being laminated to each other.

11. In goggles having a frame and a lens which define the sealed region with the face of the wearer thereof, an opening in said frame, and a membrane consisting of hydrophylic perfluorosulfonic acid polymer for fogging prevention on said frame sealing said opening.

12. The invention according to claim 11 wherein a plurality of said openings are spaced from each other along the edge defined where said frame and lens meet each other, a plurality of said membranes each, separately disposed in sealing relationship with said openings on said frame.

13. The invention as set forth in claim 11 further comprising a ring of double sided transfer tape attached to said frame around said opening, said membrane being attached to said frame via said ring.

* * * * *